(12) United States Patent
Tsao (10) Patent No.: US 8,985,771 B2
(45) Date of Patent: Mar. 24, 2015

(54) IMAGE CAPTURING APPARATUS AND CAPTURING METHOD

(71) Applicant: Altek Corporation, Hsinchu (TW)

(72) Inventor: Te-Chao Tsao, Hsinchu County (TW)

(73) Assignee: Altek Corporation, Hsinchu (TW)

(*) Notice: Subject to any disclaimer, the term of this patent is extended or adjusted under 35 U.S.C. 154(b) by 0 days.

(21) Appl. No.: 13/736,075

(22) Filed: Jan. 8, 2013

(65) Prior Publication Data

US 2014/0192320 A1   Jul. 10, 2014

(51) Int. Cl.
*A61B 3/14* (2006.01)
*A61B 3/00* (2006.01)

(52) U.S. Cl.
CPC ............... *A61B 3/14* (2013.01); *A61B 3/0025* (2013.01)
USPC ........... 351/206; 351/200; 351/205; 351/221; 351/246; 348/78

(58) Field of Classification Search
CPC .. A61B 3/0008; A61B 3/0025; A61B 3/0058; A61B 3/10; A61B 3/12; A61B 3/145; A61B 3/14555; G06K 9/605; G06K 9/62; G06K 9/6201; G06K 9/6202
USPC .................. 351/200; 382/219, 220, 221, 324; 348/78
See application file for complete search history.

(56) References Cited

U.S. PATENT DOCUMENTS

| | | | |
|---|---|---|---|
| 7,344,248 B2 | 3/2008 | Zorn et al. | |
| 2002/0025145 A1* | 2/2002 | Nanjyo | 396/18 |
| 2010/0149487 A1* | 6/2010 | Ribak | 351/206 |
| 2010/0271594 A1* | 10/2010 | Bergner et al. | 351/206 |
| 2011/0080559 A1* | 4/2011 | Goldstein et al. | 351/206 |
| 2011/0273669 A1* | 11/2011 | Abitbol et al. | 351/212 |
| 2012/0224142 A1* | 9/2012 | Cornsweet et al. | 351/206 |

FOREIGN PATENT DOCUMENTS

| | | |
|---|---|---|
| TW | 201106686 | 2/2011 |
| TW | 201216204 | 4/2012 |

* cited by examiner

*Primary Examiner* — Suchin Parihar
*Assistant Examiner* — William R Alexander
(74) *Attorney, Agent, or Firm* — Jianq Chyun IP Office (57) ABSTRACT

An image capturing apparatus including a plurality of image sensing modules and at least a light source is provided for capturing an image of an eye. Each of the image sensing modules includes an image sensor and a lens. The light source emits an illumination light, and the illumination light irradiates the eye. The eye reflects the illumination light into an image light. The image light includes a plurality of sub-image beams, and the sub-image beams are transmitted to the image sensors of the image sensing modules through the lenses of the image sensing modules, respectively. A capturing method is also provided.

17 Claims, 6 Drawing Sheets

IMAGE CAPTURING APPARATUS AND CAPTURING METHOD

BACKGROUND

1. Technical Field

The invention relates to an image capturing apparatus and a capturing method. Particularly, the invention relates to an image capturing apparatus and a capturing method for capturing an eye image.

2. Related Art

The eye is a window to a soul, and through the eyes, people can feel light and color of the world. Cone cells and rod cells in the eye used for perceiving lights and color are all located on retina of a fundus, which are unique tissues capable of converting light into physiological electric signals. Blood vessels used for supplying blood and nutrients to the eye are also located on the fundus. When the fundus has a problem of vessel proliferation or rupture, for example, has symptoms of macular degeneration and haemorrhage, etc., it is likely to cause death of the cone cells and rod cells on the retina, which may result in loss of vision of a patient. Therefore, in eye disease diagnosis and preventive health care, observation and tracking of images of the fundus are very important.

Generally, limited by a pupil size, in a single one-angle shooting of a conventional fundus image shooting method, even if pupil dilation drug such as a mydriatic agent is used, a fundus image range that can be captured is only a viewing angle of about 30 to 40 degrees. Therefore, if an image of an edge of the fundus is to be captured, the patient is asked to stare a reference point, and then the point where the eye stares is continually moved around in a slow and stable speed, so as to continually obtain a plurality of images of the fundus. Then, a data processing device such as a computer, etc. is used to synthesize the images of the fundus through specific image synthesis software. However, an illumination light used for repeatedly capturing the images of the fundus may also cause discomfort and fatigue of the eye of the patient, which may cause unconscious blink of the eye or nystagmus to influence an image capturing quality. Moreover, since the images of the fundus are obtained through multiple shoots, an exposure value and a white balance for each shooting are different, and the obtained images need to be corrected before being synthesized by a large-scale calculator such as a computer, etc., such that difficulty in correction is increased to influence the quality of the synthesized image. If the quality of the synthesized image is influenced, a medical staff is not easy to identify a microvascular image of the fundus, which may cause judgement difficulty and even delay a timing of treatment of the patient. Therefore, it is important to quickly obtain a complete and clear image of the fundus.

SUMMARY

The invention is directed to an image capturing apparatus, which is capable of capturing images of a plurality of different zones of an eye.

The invention is directed to a capturing method, by which a plurality of images of an eye are simultaneously captured from different directions for synthesis.

An embodiment of the invention provides an image capturing apparatus, which is configured to capture an image of an eye, and the image capturing apparatus includes a plurality of image sensing modules and at least one light source. Each of the image sensing modules includes an image sensor and a lens. The light source emits an illumination light, and the illumination light irradiates the eye. The eye reflects the illumination light into an image light. The image light includes a plurality of sub-image beams, and the sub-image beams are transmitted to the image sensors of the image sensing modules through the lenses of the image sensing modules, respectively.

In an embodiment of the invention, the illumination light irradiates a fundus of the eye through a pupil of the eye, the fundus reflects the illumination light into the image light, and the sub-image beams of the image light are respectively transmitted to the image sensing modules through the pupil.

In an embodiment of the invention, image capturing ranges of two adjacent image sensing modules on the fundus are partially overlapped.

In an embodiment of the invention, optical axes of the lenses of the image sensing modules are not parallel to each other, and the optical axes of the lenses pass through the pupil of the eye.

In an embodiment of the invention, each of the image sensing modules further includes an actuator, which is connected to at least one of the image sensor and the lens to focus the image sensing module.

In an embodiment of the invention, each of the image sensing modules further includes a micro processing unit, which is electrically connected to the corresponding image sensor to obtain data of an image produced by the sub-image beam detected by the image sensor.

In an embodiment of the invention, the image capturing apparatus further includes a processing unit, which is electrically connected to the image sensing modules to synthesize a plurality of images of the eye that are respectively produced by the sub-image beams detected by the image sensors.

In an embodiment of the invention, the images of the eye detected by two of the adjacent image sensors are partially overlapped.

In an embodiment of the invention, the processing unit compares the coinciding portions of the images to serve as a correction reference used when the images are synthesized.

In an embodiment of the invention, the processing unit includes a first comparison module, a second comparison module, a third comparison module, a fourth comparison module and a determination module. The first comparison module compares coinciding portions of a first peripheral image in the peripheral images and the central image. The second comparison module compares coinciding portions of a second peripheral image in the peripheral images and the central image. The third comparison module calculates an average image of coinciding portions of the first peripheral image and the second peripheral image, and compares coinciding portions of the average image and the central image. The fourth comparison module calculates a gradient image of the coinciding portions of the first peripheral image and the second peripheral image, and compares coinciding portions of the gradient image and the central image. The determination module determines a minimum comparison difference of comparison results of the first to the fourth comparison modules, where when a comparison difference of the first comparison module is the minimum, the determination module uses data of the first peripheral image for the coinciding portions of the first peripheral image and the second peripheral image; when a comparison difference of the second comparison module is the minimum, the determination module uses data of the second peripheral image for the coinciding portions of the first peripheral image and the second peripheral image; when a comparison difference of the third comparison module is the minimum, the determination module uses data of the average image for the coinciding portions of the first peripheral image and the second peripheral image;

and when a comparison difference of the fourth comparison module is the minimum, the determination module uses data of the gradient image for the coinciding portions of the first peripheral image and the second peripheral image.

In an embodiment of the invention, the processing unit first performs a correction of reducing pincushion distortion on the images of the eye, and then synthesizes the images performed with the correction of reducing pincushion distortion.

An embodiment of the invention provides a capturing method for capturing an image of an eye. The capturing method includes simultaneously capturing a plurality of images of the eye from different directions, and synthesizing the images.

In an embodiment of the invention, the images of the eye are a plurality of images of a fundus of the eye, and the step of simultaneously capturing the images of the eye from different directions includes capturing the images of the fundus of the eye through a pupil of the eye.

In an embodiment of the invention, two adjacent images of the fundus of the eye are partially overlapped.

In an embodiment of the invention, the step of synthesizing the images includes comparing the coinciding portions of the images to serve as a correction reference used when the images are synthesized.

In an embodiment of the invention, the correction reference includes at least one of a color correction reference, a coordinate conversion correction reference and a noise reduction correction reference.

In an embodiment of the invention, the images of the eye include a central image and a plurality of peripheral images adjacent to the central image.

In an embodiment of the invention, the step of synthesizing the images includes: (a) comparing coinciding portions of a first peripheral image in the peripheral images and the central image; (b) comparing coinciding portions of a second peripheral image in the peripheral images and the central image; (c) calculating an average image of coinciding portions of the first peripheral image and the second peripheral image, and comparing coinciding portions of the average image and the central image; (d) calculating a gradient image of the coinciding portions of the first peripheral image and the second peripheral image, and comparing coinciding portions of the gradient image and the central image; and (e) determining a minimum comparison difference in comparison results of the step (a) to the step (d), where when a comparison difference of the step (a) is the minimum, data of the first peripheral image is used for the coinciding portions of the first peripheral image and the second peripheral image; when a comparison difference of the step (b) is the minimum, data of the second peripheral image is used for the coinciding portions of the first peripheral image and the second peripheral image; when a comparison difference of the step (c) is the minimum, data of the average image is used for the coinciding portions of the first peripheral image and the second peripheral image; and when a comparison difference of the step (d) is the minimum, data of the gradient image is used for the coinciding portions of the first peripheral image and the second peripheral image.

In an embodiment of the invention, data of the central image is used for a central zone of the central image, and data of the peripheral images is used for portions of a surrounding zone of the central image that coincide with the central zones of the adjacent peripheral images.

In an embodiment of the invention, the capturing method further includes performing a correction of reducing pincushion distortion on the images before the images are synthesized, where the step of synthesizing the images is synthesizing the images performed with the correction of reducing pincushion distortion.

According to the above descriptions, the image capturing apparatus according to the embodiments of the invention uses a plurality of image sensing modules to respectively capture a plurality of images of the eye. In this way, time required for shooting eye images for multiple times is decreased, and the eye images of a wide viewing angle are obtained. In the capturing method according to the embodiments of the invention, a plurality of images of the eye can be simultaneously captured from different directions, and the images can be synthesized. By synthesizing the simultaneously captured images, a phenomenon of uneven brightness and contrast between the images obtained by shooting the eye for multiple times is avoided, so as to improve efficiency and accuracy for synthesizing the images.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION OF DISCLOSED EMBODIMENTS

Figure 1A:
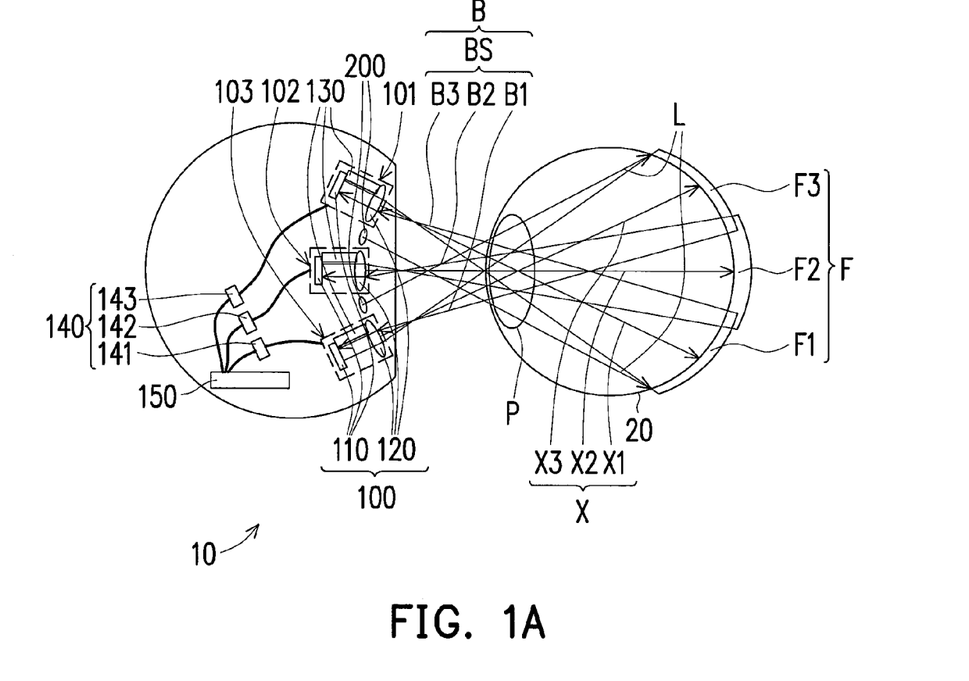
FIG. 1A is a cross-sectional view of an image capturing apparatus according to an embodiment of the invention.
Figure 1B:
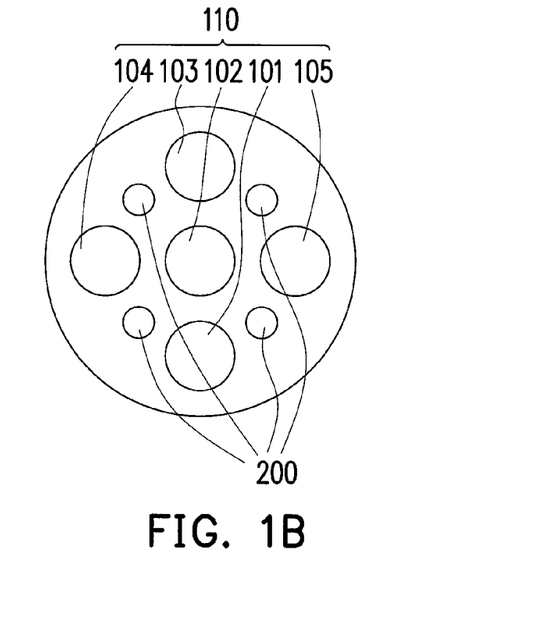
FIG. 1B is a front view of the image capturing apparatus in the embodiment of FIG. 1A.

FIG. 1A is a cross-sectional view of an image capturing apparatus according to an embodiment of the invention. FIG. 1B is a front view of the image capturing apparatus in the embodiment of FIG. 1A. Referring to FIG. 1A and FIG. 1B, in the present embodiment, the image capturing apparatus 10 is used to capture images of an eye 20. The image capturing apparatus 10 includes a plurality of image sensing modules 100 and at least one light source 200. Each of the image sensing modules 100 includes an image sensor 110 and a lens 120. The image sensor 110 can be a complementary metal-oxide-semiconductor (CMOS) sensor, a charge coupled device (CCD) or any other optical sensor adapted to receive images. Moreover, in the present embodiment, the lens 120 can be driven by a voice coil motor. In the present embodiment, the image capturing apparatus 10 includes 5 image sensing modules 101, 102, 103, 104 and 105, and in other embodiments, the image capturing apparatus 10 may include more or less image sensing modules 100 according to an actual requirement, which is not limited by the invention. Meanwhile, in the present embodiment, the image capturing apparatus 10 includes four light sources 200, and in other embodiments, the number and distribution of the light sources 200 can be designed according to an actual requirement to achieve a purpose of illumination, which is not limited by the invention. The light source 200 can be a light-emitting diode (LED) or any other suitable light-emitting device, and a light emitted therefrom is a visible light or an invisible light such as infrared, etc., which is not limited by the invention. The light source 200 emits an illumination light L, and the illumination light L irradiates the eye 20. The eye 20 reflects the illumination light L into an image light B, and the image light B includes a plurality of sub-image beams BS, and the sub-image beams BS are respectively transmitted to the image sensors 110 through the lenses 120 of the image sensing modules 100.

In detail, in the present embodiment, the illumination light L can irradiate a fundus F of the eye 20 through a pupil P of the eye 20. The fundus F reflects the illumination light L into the image light B, and the sub-image beams BS of the image light B are respectively transmitted to the image sensing modules 100 through the pupil P. Image capturing ranges of two adjacent image sensing modules 100 on the fundus F are partially overlapped. Moreover, optical axes X of the lenses 120 of the image sensing modules 100 can be unparallel to each other, and the optical axes X of the lenses 120 pass through the pupil P of the eye 20. For example, the image sensing module 101 in FIG. 1A has an optical axis X1, the image sensing module 102 has an optical axis X2, and the image sensing module 103 has an optical axis X3, where the optical axis X1, the optical axis X2 and the optical axis X3 that are not parallel to each other passes through the pupil P, such that the image sensing module 101, the image sensing module 102 and the image sensing module 103 can respectively capture images of different zones on the fundus F from different directions. Namely, the image sensing module 101 can capture an image of a fundus zone F1, the image sensing module 102 can capture an image of a fundus zone F2, and the image sensing module 103 can capture an image of a fundus zone F3. The fundus zone F1 and the fundus zone F2 are partially overlapped, and the fundus zone F2 and the fundus zone F3 are partially overlapped. In this way, the image capturing apparatus 10 can simultaneously capture images of different zones on the fundus F to aid a medical staff to study more comprehensive eye image information of a patient, so as to improve accuracy and efficiency of clinical diagnosis of the medical staff.

In detail, referring to FIG. 1A, in the present embodiment, the image sensing module 100 further includes an actuator 130, which is connected to at least one of the image sensor 110 and the lens 120 to focus the image sensing module 100. The actuator 130 can be a voice coil motor (VCM) or other types of motor. For example, in the present embodiment, the actuator 130 can drive the image sensing modules 101, 102 and 103 to respectively focus on the fundus F of the eye 20. As an eye diopter varies along with people, and even if in a same eye, the diopters of seeing the fundus from different angles through the pupil are also different, the actuator 130 is used to respectively control focusing of each of the image sensing modules 100, which is adapted to local diopter difference of the eye and is also adapted to different eyes, so as to shorten a fundus shooting time and improves the image quality.

Figure 2:
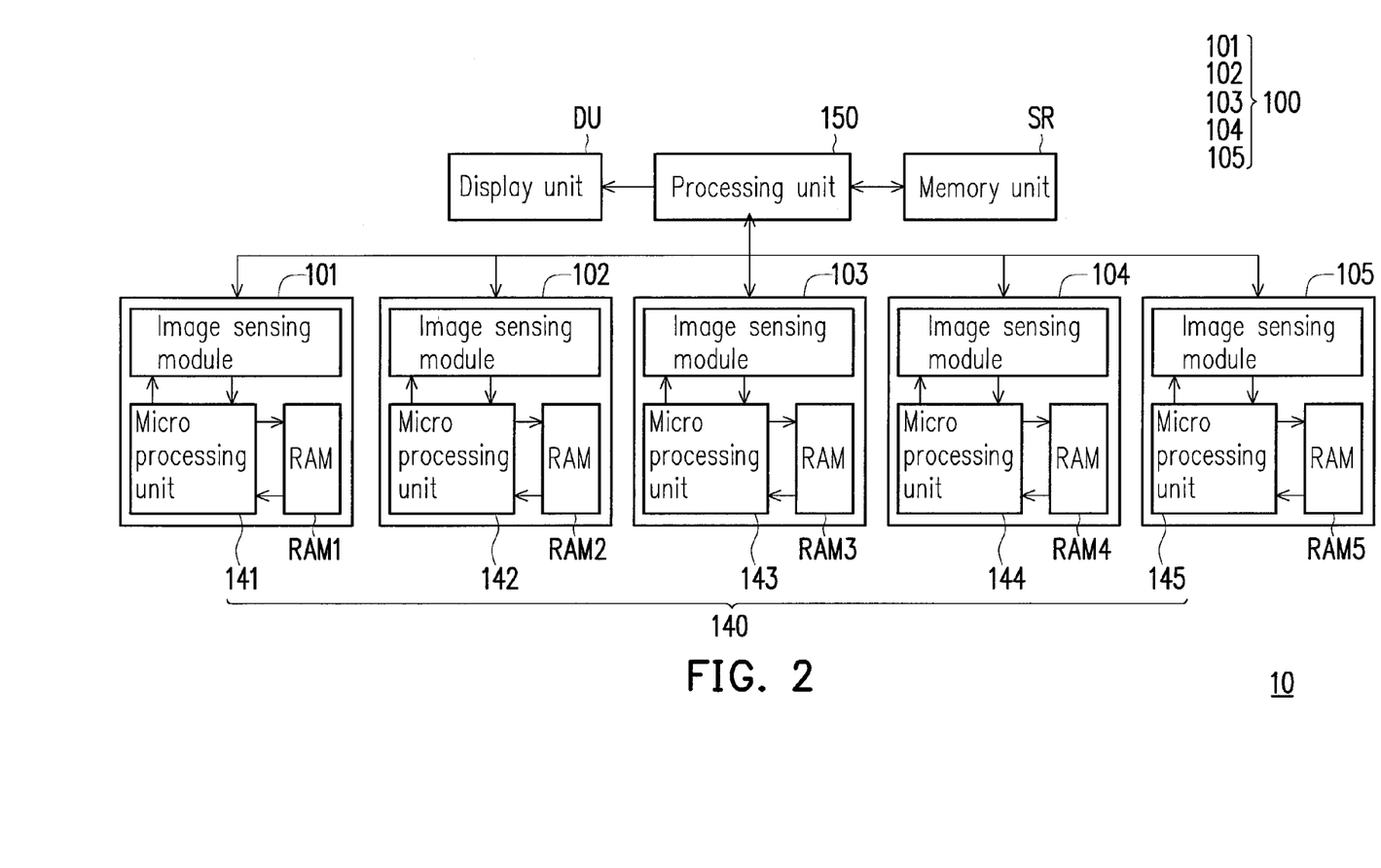
FIG. 2 is a block diagram of the image capturing apparatus in the embodiment of FIG. 1A.

Moreover, the image sensing module 100 further includes a micro processing unit 140, which is electrically connected to the corresponding image sensor 100 to obtain data of an image produced by the sub-image beam BS detected by the image sensor 100. The micro processing unit 140 is a microprocessor such as an image signal processor (ISP), etc. For example, in the present embodiment, the image sensing module 101 includes a micro processing unit 141, the image sensing module 102 includes a micro processing unit 142, and the image sensing module 103 includes a micro processing unit 143. Namely, each of the image sensing modules 100 may have the respective micro processing unit 140 to serve as a fundus image processing sub-system. Moreover, the image capturing apparatus 100 may further include a processing unit 150, which is electrically connected to the image sensing modules 100 to synthesize a plurality of images of the eye 20 that are respectively produced by the sub-image beams BS detected by the image sensors 110. The processing unit 150 can be a digital signal processor (DSP). For example, referring to FIG. 2, in the present embodiment, the image sensing modules 101, 102, 103, 104 and 105 respectively have the corresponding micro processing units 141, 142, 143, 144 and 145, and the image sensing modules 101, 102, 103, 104 and 105 also have corresponding random access memories (RAMs) RAM1, RAM2, RAM3, RAM4 and RAM5 to store image information processed by the micro processing units 141, 142, 143, 144 and 145. Moreover, the processing unit 150 may synthesize image information coming from the image sensing modules 101, 102, 103, 104 and 105 and processed by the micro processing unit 140, and may store a synthesized result or computed data in a memory unit SR, where the memory unit SR is, for example, a synchronous dynamic random access memory (SDRAM). Therefore, image synthesis efficiency is effectively increased and a high cost caused by using a fast processor is saved. Meanwhile, in the present embodiment, since the micro processing unit 140 used in collaboration with the processing unit 150 can reduce the fundus shooting time, fundus images of different zone captured from different angles can be continuously processed, and the synthesized fundus image can be displayed on a display unit DU, such that the image capturing apparatus 10 may have a live view function to assist focusing the fundus image, so as to improve efficiency and accuracy for synthesizing the images.

Figure 1C:
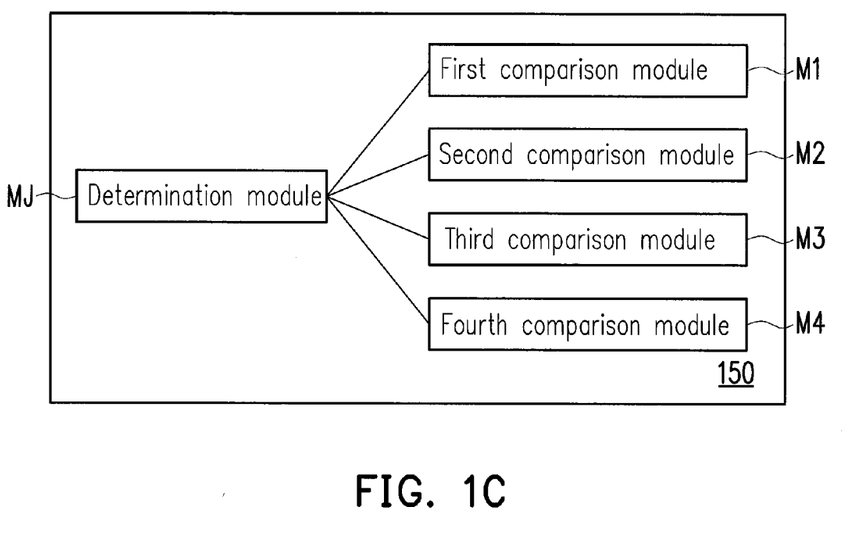
FIG. 1C is a schematic diagram of the image capturing apparatus in the embodiment of FIG. 1A.
Figure 3:
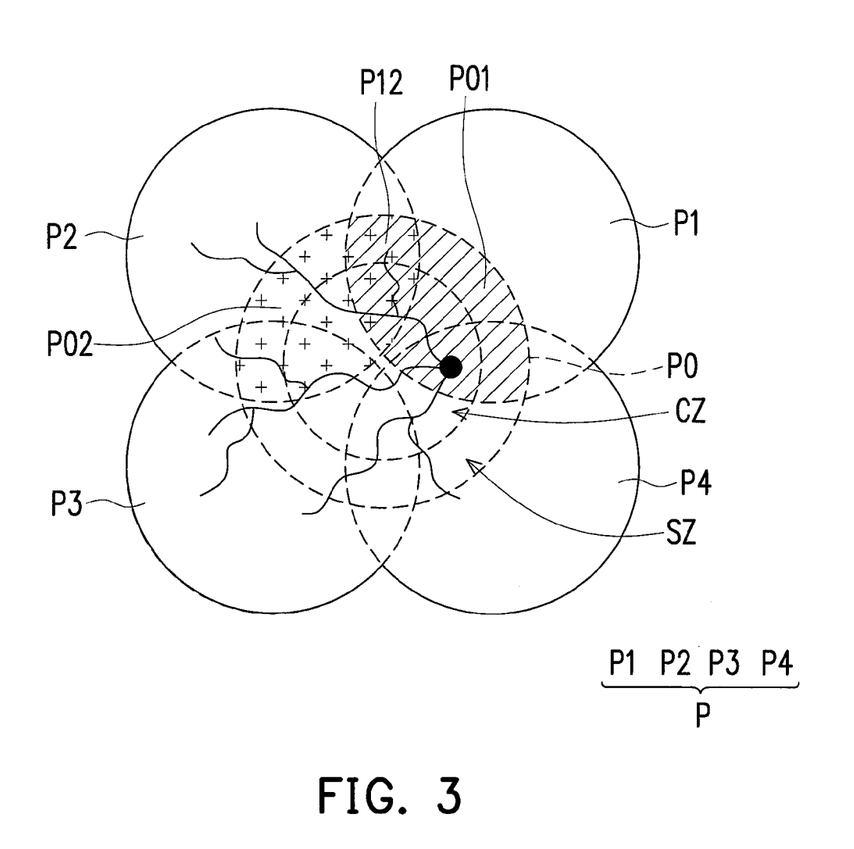
FIG. 3 is a schematic diagram of a plurality of overlapped fundus images according to the embodiment of FIG. 1A.

In detail, referring to FIG. 1A, FIG. 1B and FIG. 3, in the present embodiment, the images of the eye 20 detected by two adjacent image sensors 110 are partially overlapped, and the images of the eye 20 may include a central image P0 and a plurality of peripheral images P adjacent to the central image P0. The processing unit 150 may compare the coinciding portions of the images to serve as a correction reference used when the images are synthesized. The correction reference includes at least one of a color correction reference, a coordinate conversion correction reference and a noise reduction correction reference. In detail, referring to FIG. 1A, FIG. 1C and FIG. 3, the processing unit 150 may include a first comparison module M1, a second comparison module M2, a third comparison module M3, a fourth comparison module M4 and a determination module MJ. The first comparison module M1 compares coinciding portions of a first peripheral image P1 in the peripheral images P and the central image P0, i.e. compares data of the first peripheral image P1 in a coinciding zone P01 (i.e. a zone drawn with oblique lines) with data of the central image P0 in the coinciding zone P01. The second comparison module M2 compares coinciding portions of a second peripheral image P2 in the peripheral images P and the central image P1, i.e. compares data of the second peripheral image P2 in a coinciding zone P02 (i.e. a zone drawn with cross lines) with data of the central image P0 in the coinciding zone P02. The third comparison module M3 calculates an average image of coinciding portions of the first peripheral image P1 and the second peripheral image P2, and compares coinciding portions of the average image and the central image P0, i.e. after averaging data of the first peripheral image P1 in a coinciding zone P12 (a zone simultaneously drawn with oblique lines and cross lines) and data of the second peripheral image P2 in the coinciding zone P12, the third comparison module M3 compares the averaged data with data of the central image P0 in the coinciding zone P12. The fourth comparison module M4 calculates a gradient image of the coinciding portions of the first peripheral image P1 and the second peripheral image P2, and compares coinciding portions of the gradient image and the central image P0, i.e. after performing gradient image computation on data of the first peripheral image P1 in the coinciding zone P12 and data of the second peripheral image P2 in the coinciding zone P12, the fourth comparison module M4 compares data of a computation result thereof with data of the central image P0 in the coinciding zone P12. The determination module MJ determines a minimum comparison difference of comparison results of the first to the fourth comparison modules M1, M2, M3 and M4, where when a comparison difference of the first comparison module M1 is the minimum, the determination module MJ uses data of the first peripheral image P1 for the coinciding portions of the first peripheral image P1 and the second peripheral image P2. When a comparison difference of the second comparison module M2 is the minimum, the determination module MJ uses data of the second peripheral image P2 for the coinciding portions of the first peripheral image P1 and the second peripheral image P2. When a comparison difference of the third comparison module M3 is the minimum, the determination module MJ uses data of the average image for the coinciding portions of the first peripheral image P1 and the second peripheral image P2. When a comparison difference of the fourth comparison module M4 is the minimum, the determination module MJ uses data of the gradient image for the coinciding portions of the first peripheral image P1 and the second peripheral image P2. In this way, the images received by the image sensing module 100 can be synthesized in a manner of the minimum difference and the most correct content. Generally the central image P0 is an image close to a central zone of the fundus F, which has a distortion such as a pincushion distortion smaller than that of the image at a zone away from the central zone of the fundus F, which is easy to be corrected. As the central image P0 is taken as a reference image, and errors of the central image P0 and the other peripheral images P are referred to synthesize the images of the fundus F, accuracy of image synthesis is further enhanced. The number of the peripheral images P illustrated in FIG. 3 is only used as an example; the actually computed images can be different according to the number of the actually captured images, which is not limited by the invention.

Moreover, in the present embodiment, the central image P0 is partially overlapped with the peripheral images P (which are, for example, the first peripheral image P1, the second peripheral image P2, the third peripheral image P3 and the fourth peripheral image P4, and in other embodiments, the number of the peripheral images can be increased or decreased according to an actual requirement, which is not limited by the invention). Since the human eye has diopter, in the image of the fundus F, an image distortion at an outer edge of the image is obvious compared to that at a central portion. In the present embodiment, the processing unit 150 may use data of the central image P0 for a central zone CZ of the central image P0, and the processing unit 150 may use data of the peripheral images P for coinciding portions of the surrounding zone SZ of the central image P0 and the central zones CZ of the peripheral images P. Namely, when the images of the fundus F are synthesized, it is better to use the central portion of a single fundus image as far as possible, and avoid using the zone at the outer edge of the image that has an obvious image distortion. In the present embodiment, since the processing unit 150 can first perform a correction of reducing pincushion distortion on the images of the eye 20 for subsequent synthesis, particularly on an outer edge portion of the image that has a severe image distortion, the manner of correcting the pincushion distortion can generally add extra image points to compensate resolution decrease caused by the correction. Therefore, the method of avoiding using the image edge to synthesize the images of the fundus F can mitigate decrease of image quality caused by the additionally added image points.

The first comparison module M1, the second comparison module M2, the third comparison module M3, the fourth comparison module M4 and the determination module MJ can be programs stored in a storage medium of the image capturing apparatus 10, which can be located into the processing unit 150 to execute the aforementioned functions. Alternatively, in other embodiments, the first comparison module M1, the second comparison module M2, the third comparison module M3, the fourth comparison module M4 and the determination module MJ can also be hardware devices composed of logic circuit components, which can be used to execute the aforementioned functions.

Figure 4:
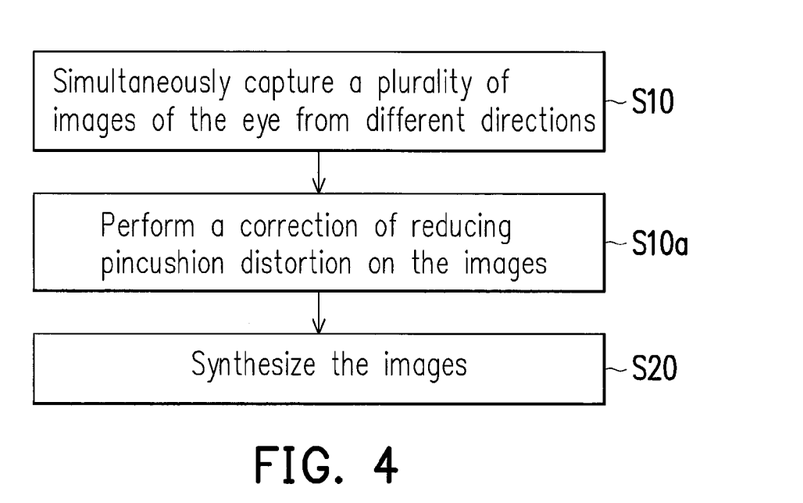
FIG. 4 is a flowchart illustrating a capturing method according to the embodiment of FIG. 1A.

FIG. 4 is a flowchart illustrating a capturing method according to an embodiment of the invention. Referring to FIG. 1A, FIG. 3 and FIG. 4, in the present embodiment, the capturing method is used to capture an image of the eye 20. The capturing method includes simultaneously capturing a plurality of images P of the eye 20 from different directions (step S10). The capturing method further includes synthesizing the images P (step S20). The images P of the eye 20 are a plurality of images P of the fundus F of the eye 20, and the step S10 of simultaneously capturing the images P of the eye 20 from different directions includes capturing the images P of the fundus F of the eye 20 through a pupil P of the eye 20. In this way, the simultaneously captured images of the fundus F have similar brightness and contrasts, which avails the subsequent image synthesis, and saves a computation time of the image synthesis and improves the quality of the synthesized image, and avails the clinical diagnosis of eye diseases.

The images of the fundus F of the eye 20 include the central image P0 and a plurality of peripheral images P adjacent to the central image P0. Moreover, the step S20 of synthesizing the images may include comparing the coinciding portions of the images to serve as a correction reference used when the images are synthesized. Moreover, in the present embodiment, before synthesizing the images, the capturing method further includes performing a correction of reducing pincushion distortion on the images (step S10a), where the step S20 of synthesizing the images is to synthesize the images performed with the correction of reducing pincushion distortion, and the effect of synthesizing the images is as that described in the embodiment of FIG. 1A, which is not repeated.

Figure 5:
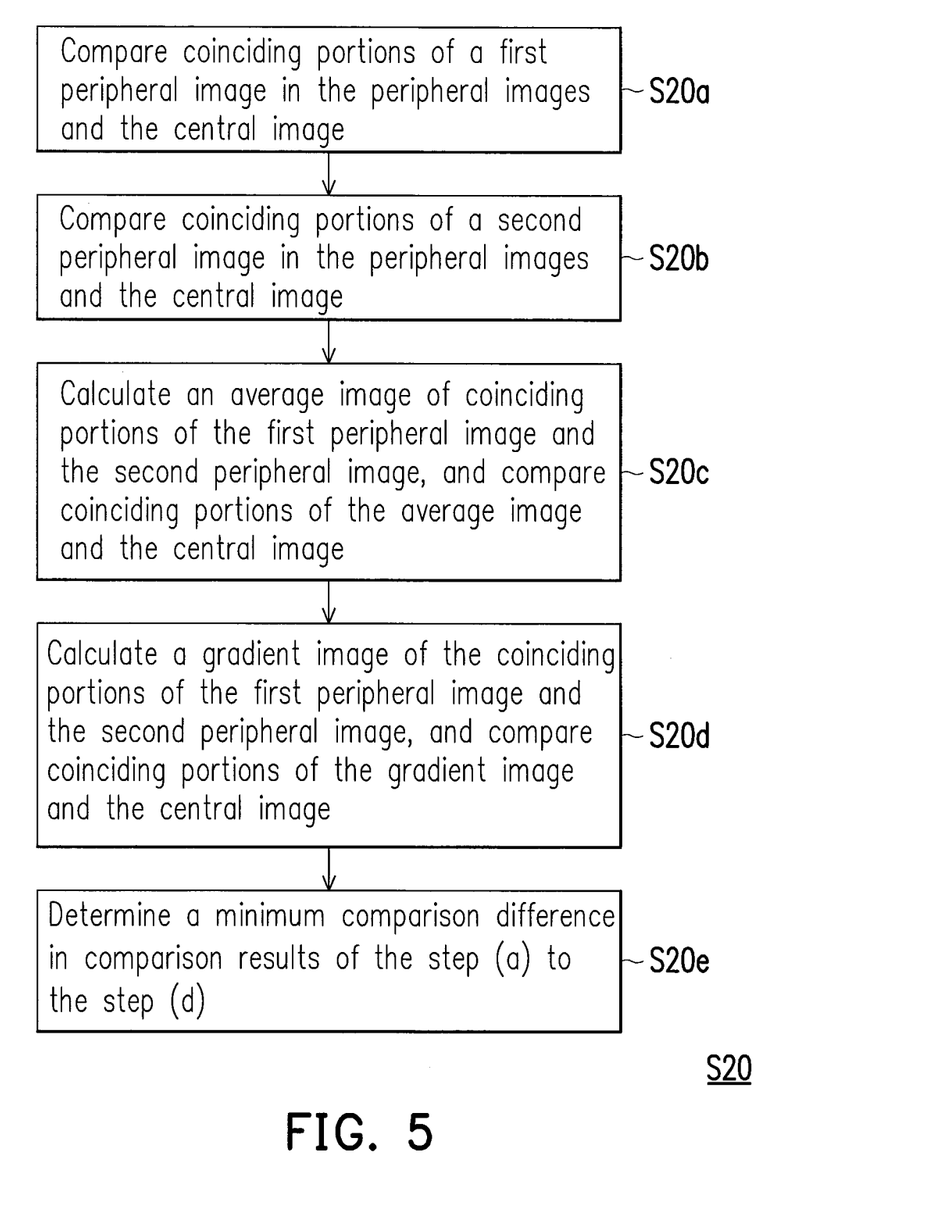
FIG. 5 is a flowchart illustrating detailed steps of a step S20 of FIG. 4.

In detail, referring to FIG. 5, the step S20 of synthesizing the images includes: (a) comparing coinciding portions of a first peripheral image P1 in the peripheral images P and the central image P0 (step S20a); (b) comparing coinciding portions of a second peripheral image P2 in the peripheral images P and the central image P0 (step S20b); (c) calculating an average image of coinciding portions of the first peripheral image P1 and the second peripheral image P2, and comparing coinciding portions of the average image and the central image P0 (step S20c); (d) calculating a gradient image of the coinciding portions of the first peripheral image P1 and the second peripheral image P2, and comparing coinciding portions of the gradient image and the central image P0 (step S20d); and (e) determining a minimum comparison difference in comparison results of the step (a) to the step (d) (step S20e). In detail, when a comparison difference of the step (a) is the minimum, data of the first peripheral image P1 is used for the coinciding portions of the first peripheral image P1 and the second peripheral image P2; when a comparison difference of the step (b) is the minimum, data of the second peripheral image P2 is used for the coinciding portions of the first peripheral image P1 and the second peripheral image P2; when a comparison difference of the step (c) is the minimum, data of the average image is used for the coinciding portions of the first peripheral image P1 and the second peripheral image P2; when a comparison difference of the step (d) is the minimum, data of the gradient image is used for the coinciding portions of the first peripheral image P1 and the second peripheral image P2. Data of the central image P0 is used for the central zone CZ of the central image P0, and data of the peripheral images P is used for coinciding portions of the surrounding zone SZ of the central image P0 and the central zones CZ of the peripheral images P. Detailed process and effect of synthesizing the images are as that described in the embodiment of FIG. 1A. The step (a) to the step (e) can be executed by the first comparison module M1, the second comparison module M2, the third comparison module M3, the fourth comparison module M4 and the determination module MJ, and details thereof can refer to descriptions of the functions executed by these modules, which are not repeated. Moreover, the sequence of the aforementioned steps is only used as an example, which is not limited by the invention.

Figure 6:
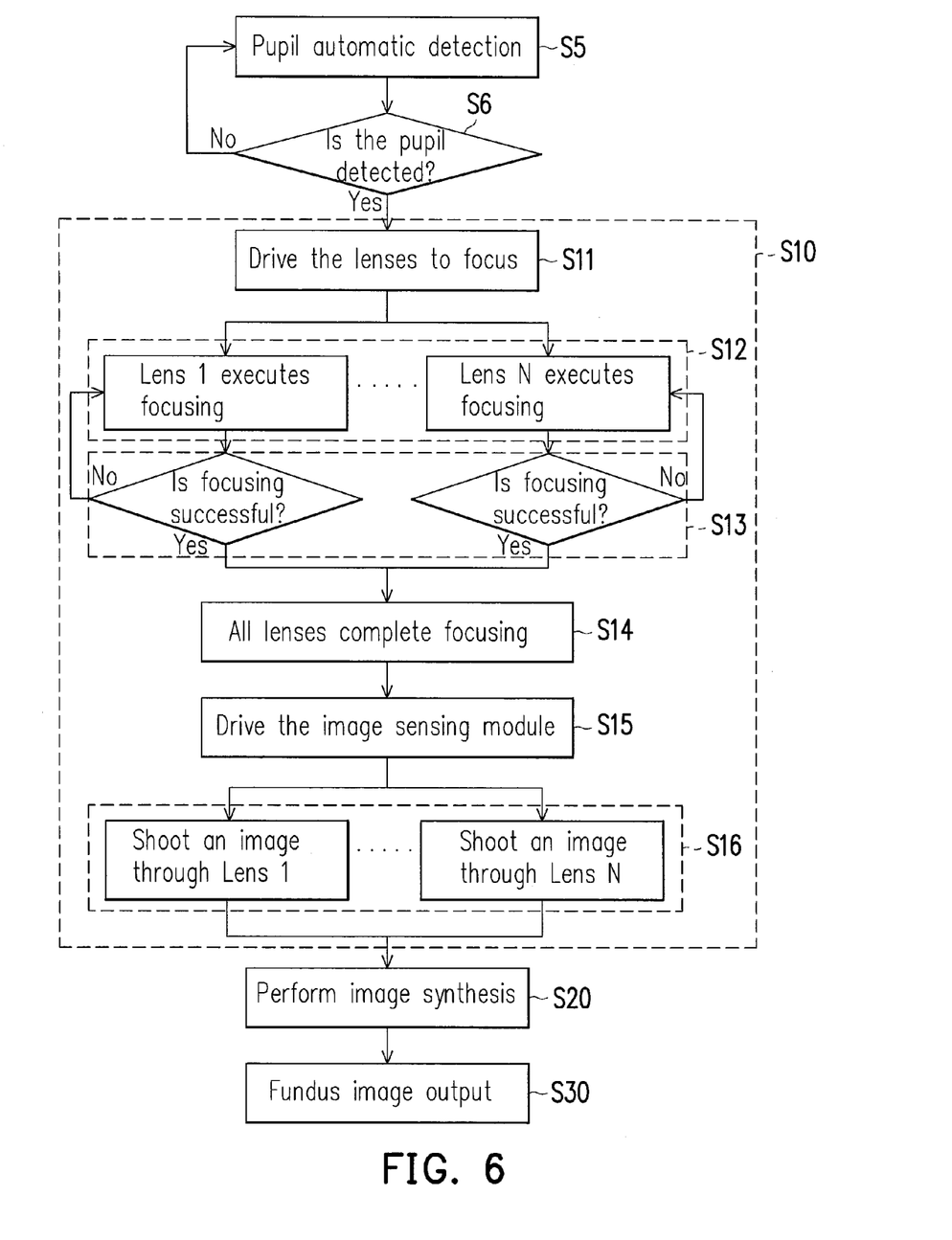
FIG. 6 is a flowchart illustrating a process of capturing a fundus image according to the embodiment of FIG. 4.

For example, referring to FIG. 6, in the present embodiment, the flow of shooting the fundus images may includes following steps. The pupil P is automatically detected (step S5), and it is determined whether the pupil P is detected (step S6), and if an image of the pupil P is not detected, the step S5 of detecting the pupil P is repeated. If the image of the pupil P is detected, a plurality of images of the eye 20 are simultaneously captured from different directions (step S10), and the lenses 120 are driven to focus (step S11). Then, the lenses 120 (for example, N lenses 120 of a lens 1, a lens 2, . . . , and a lens N, where N is a positive integer greater than 1) on the image sensing module 100 can respectively focus (step S12), and it is determined whether the focus is successful (step S13). If the focus is not successful, the step S12 is returned to again focus. After all of the lenses 120 (including the lenses 120 located at the central portion and peripheral portion of the image sensing apparatus 10) complete focusing (step S14), the image sensing module 100 is driven to capture images (step S15). The image sensing module 100 and the lens 120 can be used to capture images of the fundus F (step S16). Then, the processing unit 150 is used to synthesize the images (step S20) to output the fundus images (step S30). In this way, the image sensing apparatus 10 can automatically detect physiological information of human eye, and output a large-range and clear fundus image to facilitate medical staff to diagnose.

In summary, the image capturing apparatus according to the embodiments of the invention can be used to simultaneously capture a plurality of fundus images of different portions of the eye, and since the fundus images can be nearly simultaneously captured, the brightness and the contrasts thereof are similar. Then, the processing unit is used to compare differences of the coinciding portions of the fundus images, and the fundus images are synthesized in a manner of the minimum difference between the images, which may effectively save a time required for synthesizing the images, and quickly obtain the fundus images with a large range and good image quality. Moreover, each of the image sensing modules may include an actuator, by which the image sensing modules can simultaneously focus on different zones of the fundus from different angles, which may save a time required for capturing the eye images, decrease an eye burden of a patient and increase a success rate of capturing the large-range and clear fundus image, so as to improve medical quality and diagnosis accuracy of the medical staff.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. An image capturing apparatus, configured to capture an image of an eye, the image capturing apparatus comprising:

a plurality of image sensing modules configured to simultaneously capture a plurality of images of a fundus of the eye from different directions, each comprising an image sensor and a lens, wherein the images of the fundus of the eye comprise a central image and a plurality of peripheral images adjacent to the central image, and the central image is partially overlapped with each of the peripheral images and each overlapping portions between two peripheral images;

at least one light source, emitting an illumination light, wherein the illumination light irradiates the eye, and the eye reflects the illumination light into an image light, the image light comprises a plurality of sub-image beams, and the sub-image beams are respectively transmitted to the image sensors through the lenses of the image sensing modules; and a processing unit, electrically connected to the image sensing modules to synthesize a plurality of images of the eye that are respectively produced by the sub-image beams detected by the image sensors, wherein the processing unit comprises:

a first comparison module, comparing coinciding portions of a first peripheral image in the peripheral images and the central image;

a second comparison module, comparing coinciding portions of a second peripheral image in the peripheral images and the central image;

a third comparison module, calculating an average image of coinciding portions of the first peripheral image and the second peripheral image, and comparing coinciding portions of the average image and the central image;

a fourth comparison module, calculating a gradient image of the coinciding portions of the first peripheral image and the second peripheral image, and comparing coinciding portions of the gradient image and the central image; and a determination module, determining a minimum comparison difference of comparison results of the first to the fourth comparison modules, wherein when a comparison difference of the first comparison module is the minimum, the determination module uses data of the first peripheral image for the coinciding portions of the first peripheral image and the second peripheral image; when a comparison difference of the second comparison module is the minimum, the determination module uses data of the second peripheral image for the coinciding portions of the first peripheral image and the second peripheral image; when a comparison difference of the third comparison module is the minimum, the determination module uses data of the average image for the coinciding portions of the first peripheral image and the second peripheral image; and when a comparison difference of the fourth comparison module is the minimum, the determination module uses data of the gradient image for the coinciding portions of the first peripheral image and the second peripheral image.

2. The image capturing apparatus as claimed in claim 1, wherein the illumination light irradiates the fundus of the eye through a pupil of the eye, the fundus reflects the illumination light into the image light, and the sub-image beams of the image light are respectively transmitted to the image sensing modules through the pupil.

3. The image capturing apparatus as claimed in claim 2, wherein image capturing ranges of two adjacent image sensing modules on the fundus are partially overlapped.

4. The image capturing apparatus as claimed in claim 1, wherein optical axes of the lenses of the image sensing modules are not parallel to each other, and the optical axes of the lenses pass through the pupil of the eye.

5. The image capturing apparatus as claimed in claim 1, wherein each of the image sensing modules further comprises an actuator connected to at least one of the image sensor and the lens to focus the image sensing module.

6. The image capturing apparatus as claimed in claim 5, wherein each of the image sensing modules further comprises a micro processing unit electrically connected to the corresponding image sensor to obtain data of an image produced by the sub-image beam detected by the image sensor.

7. The image capturing apparatus as claimed in claim 1, wherein the images of the eye detected by two of the adjacent image sensors are partially overlapped.

8. The image capturing apparatus as claimed in claim 7, wherein the processing unit compares coinciding portions of the images to serve as a correction reference used when the images are synthesized.

9. The image capturing apparatus as claimed in claim 8, wherein the correction reference comprises at least one of a color correction reference, a coordinate conversion correction reference and a noise reduction correction reference.

10. The image capturing apparatus as claimed in claim 7, wherein the processing unit uses data of the central image for a central zone of the central image, and the processing unit uses data of the peripheral images for portions of a surrounding zone of the central image that coincide with central zones of the adjacent peripheral images.

11. The image capturing apparatus as claimed in claim 1, wherein the processing unit first performs a correction of reducing pincushion distortion on the images of the eye, and then synthesizes the images performed with the correction of reducing pincushion distortion.

12. A capturing method, configured to capture an image of an eye, the capturing method comprising:
   simultaneously capturing a plurality of images of a fundus of the eye from different directions, wherein the images of the fundus of the eye comprise a central image and a plurality of peripheral images adjacent to the central image, and the central image is partially overlapped with each of the peripheral images and each overlapping portions between two peripheral images; and
   synthesizing the images, wherein the step of synthesizing the images comprises comparing coinciding portions of the images to serve as a correction reference used when the images are synthesized, and the step of synthesizing the images further comprises:
   (a) comparing coinciding portions of a first peripheral image in the peripheral images and the central image;
   (b) comparing coinciding portions of a second peripheral image in the peripheral images and the central image;
   (c) calculating an average image of coinciding portions of the first peripheral image and the second peripheral image, and comparing coinciding portions of the average image and the central image;
   (d) calculating a gradient image of the coinciding portions of the first peripheral image and the second peripheral image, and comparing coinciding portions of the gradient image and the central image; and
   (e) determining a minimum comparison difference in comparison results of the step (a) to the step (d), wherein when a comparison difference of the step (a) is the minimum, data of the first peripheral image is used for the coinciding portions of the first peripheral image and the second peripheral image; when a comparison difference of the step (b) is the minimum, data of the second peripheral image is used for the coinciding portions of the first peripheral image and the second peripheral image; when a comparison difference of the step (c) is the minimum, data of the average image is used for the coinciding portions of the first peripheral image and the second peripheral image; and when a comparison difference of the step (d) is the minimum, data of the gradient image is used for the coinciding portions of the first peripheral image and the second peripheral image.

13. The capturing method as claimed in claim 12, wherein the step of simultaneously capturing the images of the fundus of the eye from different directions comprises capturing the images of the fundus of the eye through a pupil of the eye.

14. The capturing method as claimed in claim 13, wherein two adjacent images of the fundus of the eye are partially overlapped.

15. The capturing method as claimed in claim 12, wherein the correction reference comprises at least one of a color correction reference, a coordinate conversion correction reference and a noise reduction correction reference.

16. The capturing method as claimed in claim 14, wherein data of the central image is used for a central zone of the central image, and data of the peripheral images is used for portions of a surrounding zone of the central image that coincide with the central zones of the adjacent peripheral images.

17. The capturing method as claimed in claim 12, further comprising:
   performing a correction of reducing pincushion distortion on the images before the images are synthesized, wherein the step of synthesizing the images is synthesizing the images performed with the correction of reducing pincushion distortion.

* * * * *